United States Patent [19]
Sullivan

[11] Patent Number: 6,039,044
[45] Date of Patent: Mar. 21, 2000

[54] GAS DELIVERY MASK

[75] Inventor: Colin E. Sullivan, Birchgrove, Australia

[73] Assignee: University of Sydney, Sydney, Australia

[21] Appl. No.: 08/860,843

[22] PCT Filed: Dec. 8, 1995

[86] PCT No.: PCT/AU95/00830

§ 371 Date: Sep. 2, 1997

§ 102(e) Date: Sep. 2, 1997

[87] PCT Pub. No.: WO96/17643

PCT Pub. Date: Jun. 13, 1996

[51] Int. Cl.⁷ .................................................. A62B 18/02
[52] U.S. Cl. ................. 128/205.25; 128/206.24
[58] Field of Search ........................ 128/205.25, 206.21, 128/206.24, 206.26, 206.27, 206.28, 207.13

[56] References Cited

U.S. PATENT DOCUMENTS

| | | |
|---|---|---|
| 844,097 | 2/1907 | Caldwell . |
| 1,048,491 | 12/1912 | Butcher . |
| 1,206,045 | 11/1916 | Smith . |
| 1,635,275 | 7/1927 | Johnson . |
| 1,653,572 | 12/1927 | Jackson . |
| 2,241,535 | 5/1941 | Boothby et al. . |
| 2,415,846 | 2/1947 | Randall . |
| 2,578,621 | 12/1951 | Yant . |
| 2,706,983 | 4/1955 | Matheson et al. ................. 128/206.17 |
| 2,765,788 | 10/1956 | Raiche . |
| 2,931,356 | 4/1960 | Schwarz . |
| 3,330,273 | 7/1967 | Bennett . |
| 3,330,274 | 7/1967 | Bennett . |
| 3,725,953 | 4/1973 | Johnson et al. . |
| 4,274,406 | 6/1981 | Bartholomew ..................... 128/206.21 |
| 4,337,767 | 7/1982 | Yahata . |
| 4,506,665 | 3/1985 | Andrews et al. .................. 128/205.25 |
| 4,559,940 | 12/1985 | McGinnis . |
| 4,655,213 | 4/1987 | Rappoport et al. . |
| 4,782,832 | 11/1988 | Trimble et al. . |
| 4,809,692 | 3/1989 | Nowacki et al. . |
| 4,919,128 | 4/1990 | Kopala et al. . |
| 4,944,310 | 7/1990 | Sullivan . |
| 5,121,745 | 6/1992 | Israel . |
| 5,243,971 | 9/1993 | Sullivan et al. . |
| 5,647,357 | 7/1997 | Barnett et al. ..................... 128/205.25 |

FOREIGN PATENT DOCUMENTS

| | | |
|---|---|---|
| 34722/58 | 1/1958 | Australia . |
| 77110/91 | 11/1991 | Australia . |
| 0 602 424 | 11/1993 | European Pat. Off. . |
| 207751 | 3/1909 | Germany . |
| 925081 | 3/1955 | Germany .......................... 128/206.21 |
| 1104122 | 4/1961 | Germany . |
| 2652128 | 12/1977 | Germany .......................... 128/206.28 |
| 3707952 | 9/1988 | Germany . |
| 492723 | 9/1938 | United Kingdom . |
| 621010 | 4/1949 | United Kingdom .............. 128/205.25 |
| 697762 | 9/1953 | United Kingdom . |
| 775911 | 5/1957 | United Kingdom . |
| 848215 | 9/1960 | United Kingdom . |
| 1360632 | 7/1974 | United Kingdom . |
| 1467828 | 3/1977 | United Kingdom . |

*Primary Examiner*—Aaron J. Lewis
*Attorney, Agent, or Firm*—Holland & Hart LLP

[57] ABSTRACT

A mask for use in delivering gas to a user and which accommodates relative movement of a connecting gas supply line. The mask has a face contacting portion (28) which is shaped to define a chamber (29) through which gas is delivered to the respiratory tract of the user and, in a preferred form of the mask, the face contacting portion (28) is formed with a convex end region (30) which is arranged in use of the mask to be depressed by and to accommodate facial features of the user. A gas supply port (27) is formed integrally with a wall portion (35) of the chamber (29) and the port provides for connection of a supply of pressurized gas to the interior of the chamber. The mask is characterised in that the wall portion (35) that contains the gas supply port (27) is formed to exhibit a degree of flexibility that is greater than that of adjacent regions of the mask, whereby any movement that is referred to the mask by the connecting gas supply line will be accommodated, at least in part, by flexing the wall portion (35) that contains the gas supply port (27).

11 Claims, 5 Drawing Sheets

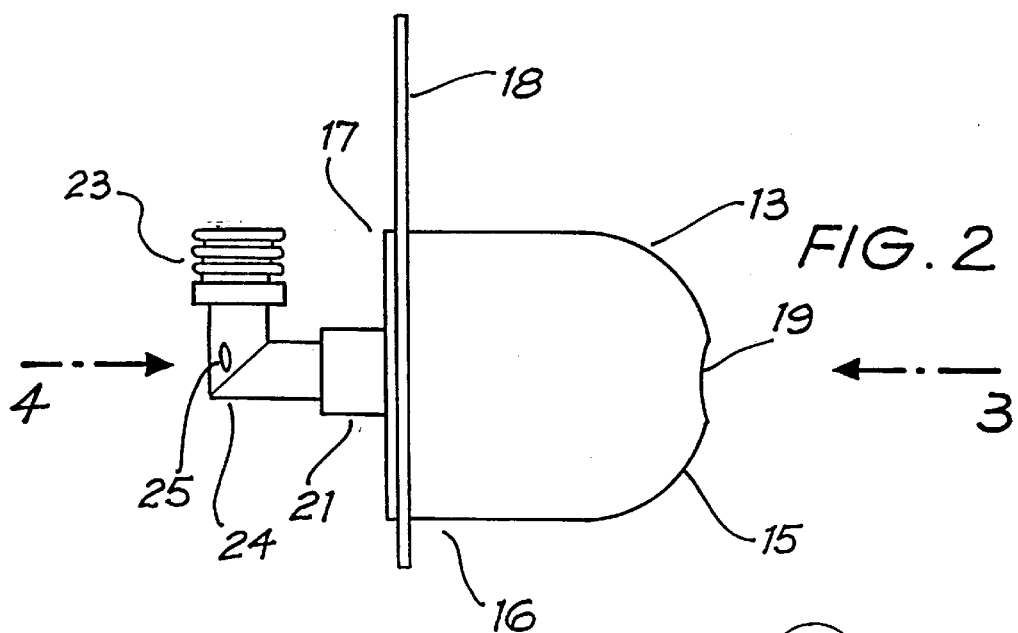
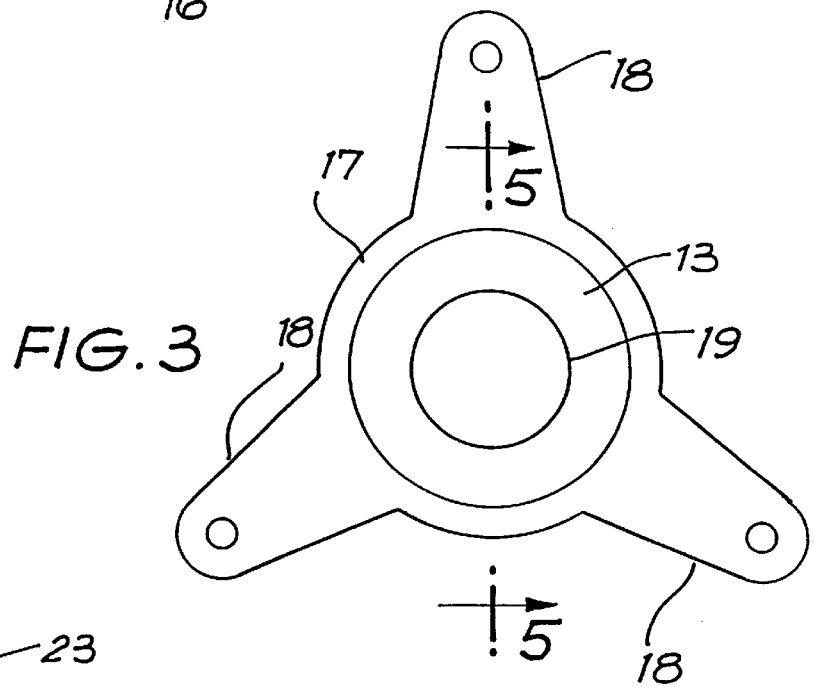
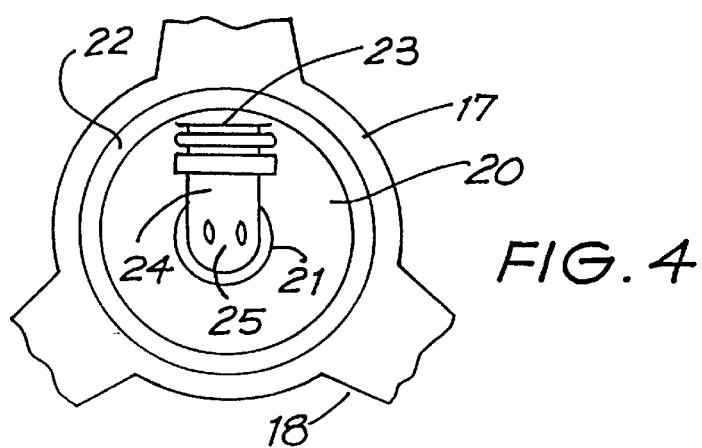

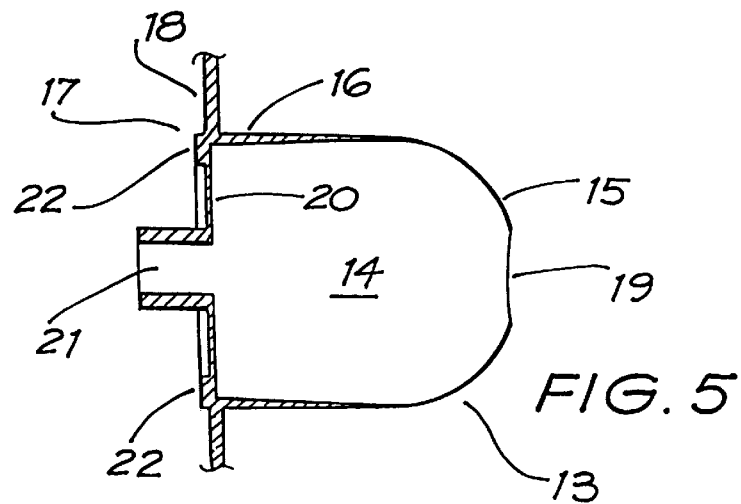
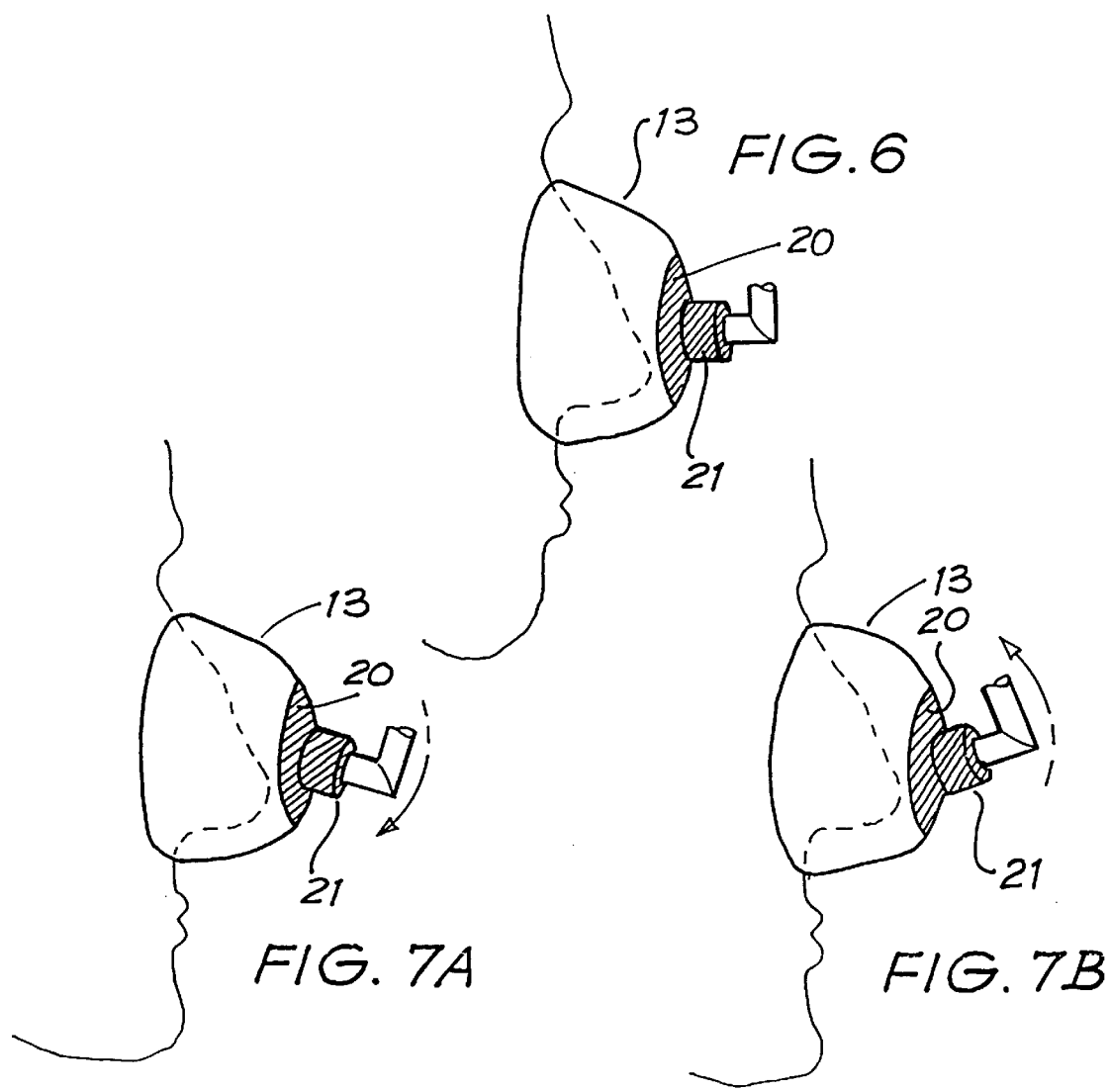

GAS DELIVERY MASK

TECHNICAL FIELD

This invention relates to a mask for use in delivering gas to a person and, in particular, to a mask which accommodates relative movement of a connecting gas supply line. The mask has been developed for use in delivering air under continuous positive pressure to the nasal passages of a person who suffers from sleep apnea and the invention is hereinafter described in the context of a mask which is suitable for such a purpose. However, it is to be understood that the invention does have broader application, for example to masks which are suitable for use in assisting breathing, for providing anaesthetic gases and for delivering resuscitation gases to subjects. Also, whilst the invention is herein described in the context of a nasal mask, it will be understood that the invention does have application to masks that are shaped to cover the mouth and/or nasal passages of a user.

BACKGROUND ART

Nasal masks which are intended to be used for delivering air under continuous positive pressure to sleeping persons ideally are required to exhibit seemingly incompatible characteristics. They should provide a complete peripheral seal around the region of contact with wearers' faces and, in order to do so, accommodate the vastly different facial features of different persons. They should be capable of maintaining the peripheral seal for prolonged periods of time, throughout the night for persons using the masks in the treatment of sleep apnea, and accommodate significant degrees of conscious and semi-conscious movement on the part of wearers. Finally, the masks should be sufficiently comfortable to enable wearers to enjoy natural sleep and, thus, should intrude as little as possible on the feeling of well being of a user.

A nasal mask which goes a long way toward meeting these requirements and which has received widespread approval from both medical advisers and users is disclosed in Australian Patent No. 643994, dated May 16, 1991, granted to The University of Sydney. This mask is radically different from prior art masks which rely on peripheral sealing, in that it incorporates a face contacting portion which is formed from an elastomeric material and which is shaped to define a balloon-like chamber. When gas is admitted to the chamber it tends to balloon outwardly and, when fitted to a wearer, the face contacting portion is caused to overlie a region of the wearer's face and seal three-dimensionally with the contours of the overlayed region.

For practical reasons, the above described mask is in use mounted to or integrated with a rigid shell-like moulding which does not (or need not) contact the wearer's face. The shell is provided to enable a gas supply line to be connected to the mask, to facilitate fastening of the mask to a user's face and to minimise the risk that movement of the gas supply line will disrupt the seal between the mask and the wearer's face. However, it has now been determined that, whilst the shell does provide a stabilising connection for the gas supply line, any force that is exerted on the shell by the gas supply line will tend to be transmitted to the mask itself, primarily because of the rigidness of the shell. Also, because the shell is interposed between the mask and the gas supply line, any lateral movement of the supply line will be amplified by an amount proportional to the distance between the mask sealing region and the point of connection with the supply line.

The present invention seeks to minimise these difficulties by providing a mask which avoids the need for a rigid shell-like moulding to be interposed between the mask itself and the gas supply line.

DISCLOSURE OF THE INVENTION

Thus, the invention may broadly be defined as providing a mask for use in delivering gas to a user and which comprises a face contacting portion which is shaped to define a chamber through which gas is delivered to the respiratory tract of the user. A gas supply port is formed integrally with a wall of the chamber and provides for connection of a supply of pressurised gas to the interior of the chamber, and means are provided to permit the mask to be secured to the user. The mask is characterised in that a portion of the wall containing the gas supply port is formed to exhibit a degree of flexibility that is greater than that of adjacent regions of the mask, whereby any movement that is referred to the mask by a connecting gas supply line will be accommodated at least in part by flexing the wall portion that contains the gas supply port.

The face contacting portion of the mask preferably is formed from an elastomeric material. Also, the chamber preferably is formed with a convex end region which is arranged in use of the mask to be depressed by and accommodate facial projections of the user, and the end region will then be formed with an aperture through which the gas is delivered to the respiratory tract of the user. When the mask is in this form and the mask is secured to the user, the end region of the chamber will be caused to overlay a region of the user's face and seal three dimensionally with contours of the overlayed region under the influence of gas delivered to the chamber.

The wall portion that contains the gas supply port is preferably formed with a thickness that is less than that of adjacent portions of the mask, so that movement of the connecting gas supply line will tend to flex the thin-wall portion and so minimise referral of movement to the body of the mask in contact with the face of the user. However, other methods of introducing flexibility into the wall portion that contains the gas supply port may be employed. For example, the wall portion may be formed with material in excess of functional requirements, such as in the form of a bulb shape or in the manner of a bellows, so that movement of the connecting gas supply line will tend to flex the excess material and so minimise referral of movement from the gas supply line to the body of the mask in contact with the face of the user.

By forming the mask in the above defined manner and s obviating the need for a shell-like portion, the mask may be made physically smaller than that which is described in the above mentioned Australian Patent No. 643994, and any movement that is referred to the face contacting portion of the mask will be amplified to a lesser extent than it is in the prior art mask.

The means that are provided to permit the mask to be secured to the wearer preferably include integrally formed securing means which are connectable to a harness. Such means preferably comprise limbs which are formed to project radially outwardly from the mask and they are arranged such that they may be positioned against the wearer's face when the mask is secured to the wearer. With this preferred construction the entire mask, including the securing means and the harness, may be positioned close to the wearer's face, so as to minimise the potential for movement of the mask relative to the wearer's face.

The invention will be more fully understood from the following description of exemplary embodiments of nasal masks. The description is provided with reference to the accompanying drawings.

BRIEF DESCRIPTION OF THE DRAWINGS

In the drawings

FIG. 2 shows a side view of the mask according to a first embodiment of the present invention, FIG. 3 shows a front view of the mask shown in FIG. 2, as viewed in the direction of arrow 3 shown in FIG. 2, FIG. 4 shows a rear view of the mask as illustrated in FIG. 2, as viewed in the direction of arrow 4 shown in FIG. 2, FIG. 5 shows a sectional elevation view of the mask as illustrated in FIG. 2 as viewed in the direction of section plane 5—5 shown in FIG. 3, FIG. 6 shows diagrammatically the manner in which the mask as illustrated in FIGS. 2 to 5 is fitted to a user, FIGS. 7A and B show in a diagrammatic manner a characteristic feature of the mask as illustrated in FIGS. 2 to 4.

MODES FOR CARRYING OUT THE INVENTION

Figure 1A:
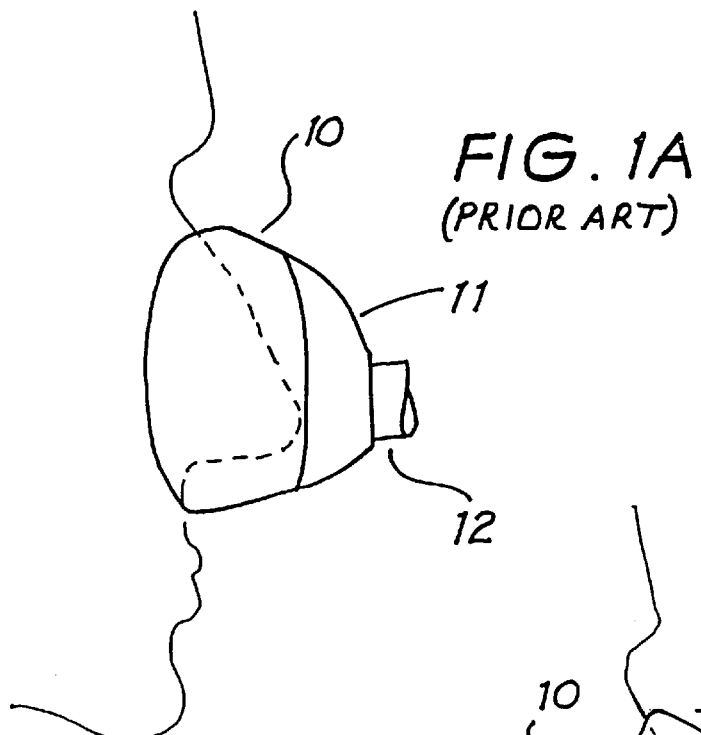
FIGS. 1A, 1B and 1C show diagrammatic representations of a prior art mask fitted to a user.
Figure 1B:
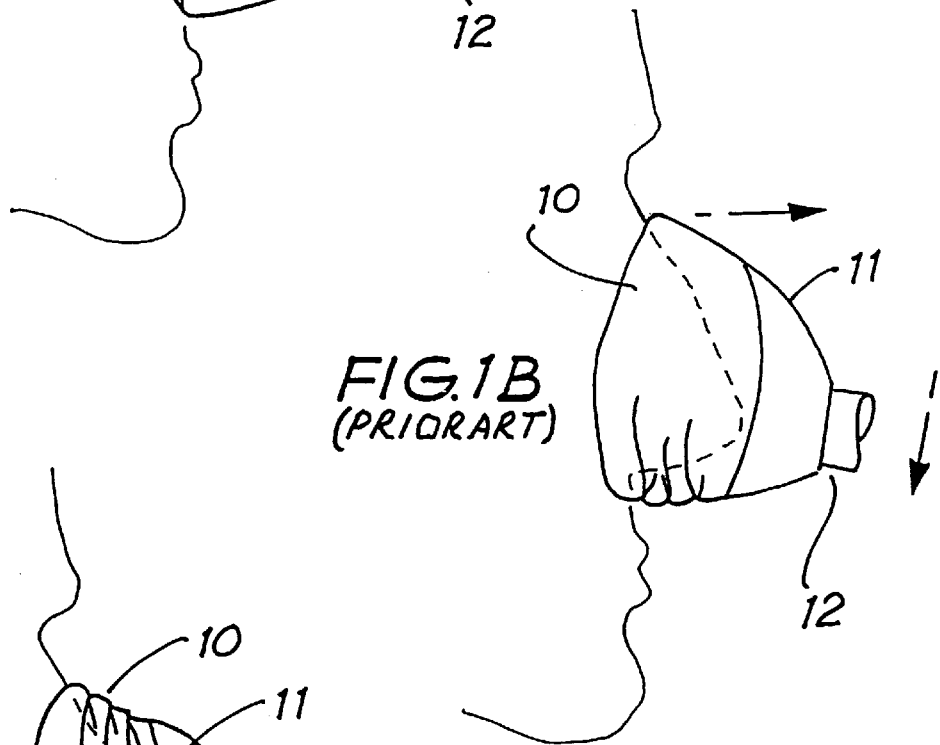
Figure 1C:
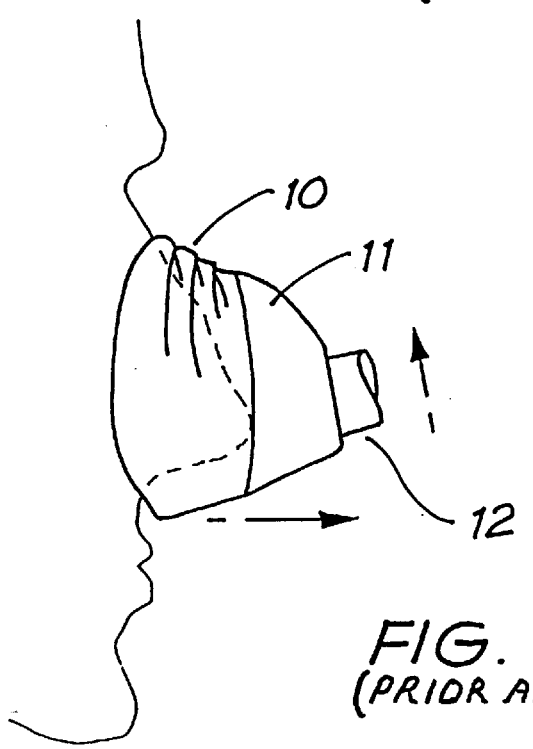
Figure 8:
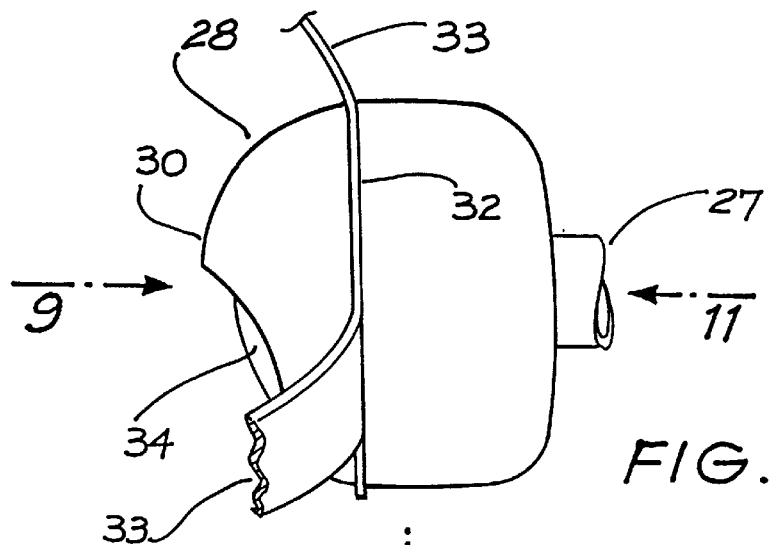
FIG. 8 shows a side view of a mask according to a second embodiment of the invention.

The prior art nasal mask which is shown diagrammatically in FIGS. 1A to C has a face contacting portion 10 which is formed from an elastomeric material and which is shaped normally to define a balloon-like chamber. The face contacting portion is mounted to a rigid shell-like moulding 11 to which an air supply line 12 is connected. When air is admitted to the chamber and the mask is fitted to the user, the face contacting portion 10 is caused to overlay contours of the user's face and seal against the overlayed region. As hereinbefore stated, a difficulty with this type of prior art mask is that relative movement between the gas delivery line 12 and the mask itself is imparted to the face conforming region of the mask by way of the rigid shell moulding. This in turn causes localised lifting of the mask from the user's face and breakage of the all-important seal between the mask and the user. Two different lifting movements are illustrated in FIGS. 1B and 1C of the drawings.

The present invention is directed to minimisation of this problem and reference is now made to FIGS. 2 to 5 which illustrate a first embodiment of a nasal mask in accordance with the present invention.

As shown in FIGS. 2 to 5, the nasal mask is formed from an elastomeric material, typically a high tear resistant silicone elastomer such as Silastic (Registered Trade Mark, Dow Corning Corporation) or Santoprene (Registered Trade Mark, Monsanto Co.). The mask comprises a face contacting portion 13 which, like the abovementioned prior art mask, is shaped to define a balloon-like chamber 14. The chamber has a generally convex end region 15 which is defined by a thin wall and which is arranged in use of the mask to be depressed by and to accommodate the nose of the user.

The convex end region 15 of the mask projects from a generally cylindrical rearward region 16 which has a slightly thicker wall than that of the convex end region. The convex end region of the mask has a thickness which preferably is not greater than 0.8 mm and most preferably has a thickness in the order of 0.2 mm or less. The relatively thicker rearward region 16 has a wall portion which increases in thickness with distance from the convex end 15 and has an average thickness in the order of 2.0 mm.

The entire face contacting portion 13 of the mask is moulded integrally with a flange 17 from which three radially projecting, flexible limbs 18 extend. The limbs 18 provide connecting points for a harness (not shown) which normally is provided to hold the mask in place on the user.

The convex end region 15 of the mask is formed with an aperture 19 through which gas is delivered to the nasal passages of the user.

The rearward end of the chamber 14, that is the end remote from the convex end of the chamber, is defined in part by a wall 20 which lies in approximately the same plane as the limbs 18, and a cylindrical walled supply port 21 is formed integrally with the wall 20. The outer margin of the wall 20 is surrounded by a peripheral rim 22 and, thus, the wall portion 20 between the rim 22 and the port 21 has a thickness that is less than that of the adjoining parts of the mask. The wall portion 20 preferably has a thickness of the same order as that of the convex end region 15.

Thus, the wall 20 containing the gas supply port 21 is formed to exhibit a degree of flexibility that is greater than that of the adjacent regions of the mask, so that any movement that may be referred to the mask by a connecting gas supply line 23 (FIG. 4) will be accommodated at least in part by flexing the wall portion 20 that contains the gas supply port. This is illustrated diagrammatically in FIGS. 7A and B of the drawings, which show how movement of the gas supply line 23 is accommodated by what might be regarded as a flexible coupling between the gas supply line and the face contacting portion 13 of the mask.

As shown in FIG. 4 the gas supply line 23 is connected to the cylindrical wall of the port 21 by way of an elbow 24. Apertures 25 are provided in the elbow to permit exhalation of gas which is exhaled by the user during normal breathing. That is, gas is inhaled from the gas supply line 23 by way of the face contacting portion 13 of the mask and then is exhaled through the ports 25, again by first passing through the face contacting portion of the mask.

The embodiment of the mask that is shown in FIGS. 8 to 11 is similar to that shown in FIGS. 2 to 6, but it has a less sharp transition between a wall portion 26 (that contains a gas supply port 27) and the remaining portion of the mask.

The mask comprises a face contacting portion 28 which is shaped to define a balloon-like chamber 29. The chamber has a generally convex end region 30 which is defined by a thin wall portion and which is arranged to be depressed by and to accommodate the nose of a wearer in the same manner as the previously described embodiment of the mask.

The convex end region 30 of the mask projects forwardly from a generally hemispherical rearward region 31 which blends into the rearward wall portion 26. The rearward region 31 has a wall thickness which progressively increases relative to that of the convex end region 30. Thus, the convex end region 30 may have a wall thickness in the range 0.2 to 0.8 mm and the rearward region 31 may have an average thickness in the order of 1.5 to 3.5 mm.

Figure 9:
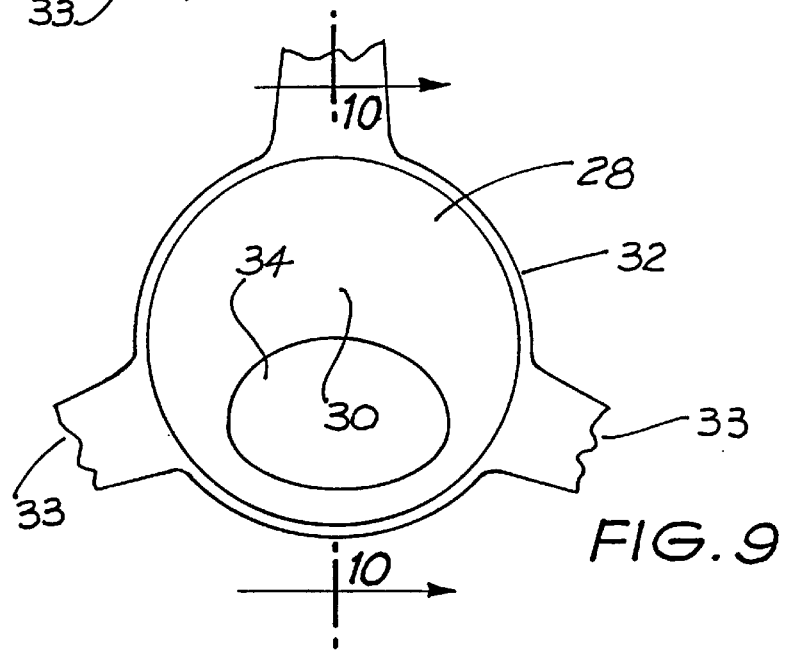
FIG. 9 shows a front view of the mask that is illustrated in FIG. 8, as viewed in the direction of arrow 9 in FIG. 8.
Figure 10:
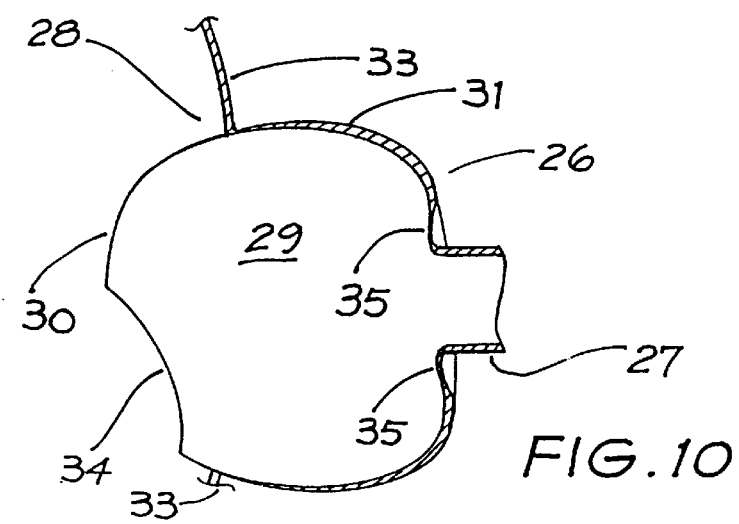
FIG. 10 shows a sectional elevation view of the mask as illustrated in FIG. 8, as viewed in the direction of section plane 10—10 shown in FIG. 9.
Figure 11:
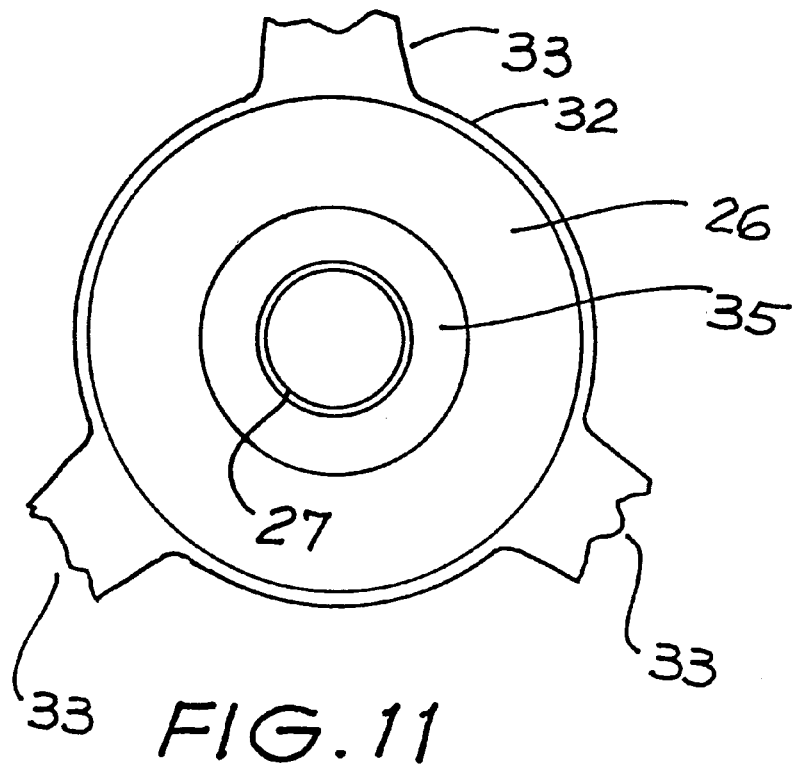
FIG. 11 shows a rear view of the mask as illustrated in FIG. 8, as seen in the direction of arrow 11 in FIG. 8.

A small flange 32 is moulded integrally with and extends around the main body of the mask and three radially projecting limbs 33 are moulded to project outwardly from the flange. As in the case of the previously described embodiment, the limbs 33 provide connecting points for a harness (not shown) which is employed for holding the mask in place on the face of a user. However, in contrast with the previously described embodiment, the flange 32 and limbs 33 as shown in FIG. 10 are positioned immediately behind the convex end region 30 of the mask, so that they will be positioned against the face of a user when the mask is placed in its intended working position. Thus, the mask as illustrated in FIGS. 8 to 11 will fit even more snugly than that which is illustrated in FIGS. 2 to 5.

The convex end region 30 of the mask is formed with an aperture 34 through which gas is delivered to the nasal passages of a user and, as indicated previously, gas is supplied to the chamber 29 by way of the supply port 27. When gas is admitted to the chamber and the mask is pushed (or held) against the wearer's face, the convex end region 30 is caused to overlay the covered area of the face and to seal three-dimensionally with contours of the overlayed area.

In order to accommodate unwanted flexing movement of the gas supply port 27 relative to the remaining portion of the mask, the rearward wall portion 26 is formed with a thickness that is reduced in an annulus 35 that surrounds the port 27. Thus, the wall portion forming the annulus may be formed with a thickness that approximates that of the convex end region 30 and, in any case, with a thickness which is significantly less than that of the adjacent wall portion 26.

Figure 12:
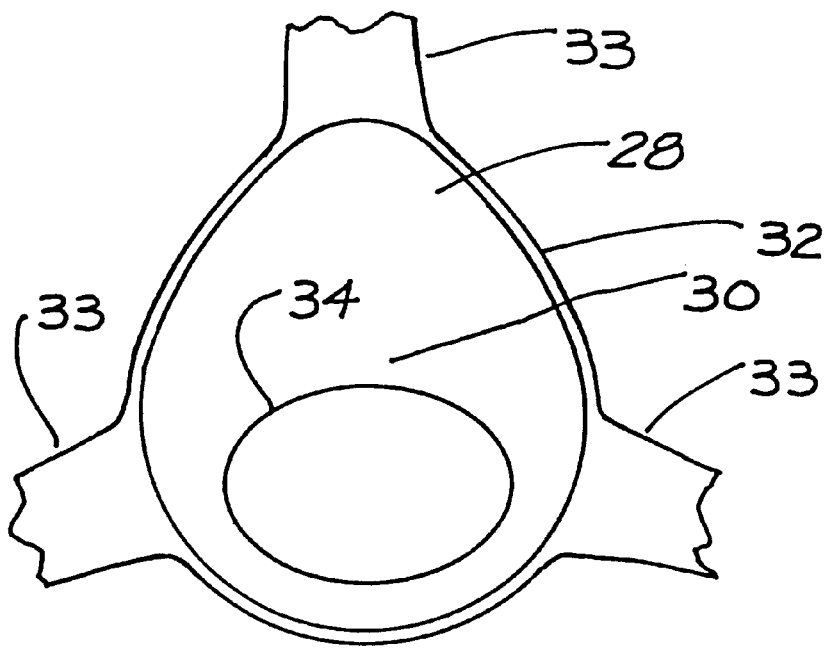
FIG. 12 shows a front view of a mask according to a third embodiment of the invention.

Variations and modifications may be made in the above described embodiments of the invention. For example, the mask may be shaped with an ovoid or other cross-section so as to conform more closely with the shape of a wearer's nose. FIG. 12 shows such a shaping and it may be compared with that which is illustrated in FIG. 9. The same reference numerals are used to identify like parts in FIGS. 9 and 12.

In a further modification of the mask which is illustrated in FIGS. 8 to 12, the gas supply port 27 may be arranged such that it enters the end wall 26 or the surrounding wall 31 in a radial or tangential direction, in which cases a region of reduced wall thickness will be provided to surround the region of entry. Additionally, the gas supply port might be positioned along one of the limbs 33, or one or more of the limbs 33 might be formed with a hollow interior such that it will function also as the gas supply port.

I claim:

1. A mask for use in delivering gas to a user and which comprises:

a face contacting portion which is formed from an elastomeric material and which is shaped to define a chamber, the chamber having a convex end region which is arranged in use of the mask to be depressed by and accommodate facial projections of the user, and the end region being formed with an aperture through which gas is delivered to the respiratory tract of the user;

a gas supply port formed integrally with a wall of the chamber and providing for connection of a supply of pressurized gas to the interior of the chamber; and means which permit the mask to be secured to the user in a manner to cause the end region of the chamber to overlay a region of the user's face and seal three-dimensionally with contours of the overlayed region under the influence of gas delivered to the chamber; the mask being characterized in that a portion of the wall containing the gas supply port is formed with a thickness that is less than that of adjacent regions of the wall of the chamber and, as a consequence, exhibits a degree of flexibility that is greater than that of adjacent regions of the mask, whereby any movement that is referred to the mask by a connecting gas supply line will be accommodated at least in part by flexing the wall portion that contains the gas supply port.

2. The mask as claimed in claim 1 wherein the wall portion that contains the gas supply port is formed with an annulus that surrounds the gas supply port and wherein the annulus is formed with the wall portion having a thickness that is less than that of the adjacent regions of the wall of the chamber.

3. The mask as claimed in claim 1 wherein the gas supply port is positioned so as to direct gas toward the convex end region of the chamber.

4. The mask as claimed in claim 1 wherein the mask has a forward portion which includes the convex end region of the chamber and a rearward portion which includes the wall portion that contains the gas supply port, and wherein the rearward portion has a wall thickness which is on average greater than the wall thickness of the forward portion.

5. The mask as claimed in claim 4 wherein the wall thickness of the rearward portion increases progressively with distance away from the forward portion.

6. The mask as claimed in claim 1 wherein the means which permit the mask to be secured to the user comprise securing means which are formed integrally with a wall surrounding the chamber and which are arranged for connection with a harness which is employed in use of the mask to secure the mask to a wearer.

7. The mask as claimed in claim 6 wherein the securing means comprise radially projecting flexible limbs and wherein the limbs are arranged for connection with the harness which is employed in use of the mask to secure the mask to a wearer.

8. The mask as claimed in claim 6 wherein the securing means are positioned to radiate outwardly from a peripheral region of the mask that is adjacent the junction of the forward and rearward portions of the mask.

9. The mask as claimed in claim 8 wherein the limbs are positioned and formed with a thickness such as to permit the limbs to bend and contact the face of the wearer when the mask is fitted to the wearer.

10. The mask as claimed in claim 9 wherein the chamber has a generally circular cross-section.

11. The mask as claimed in claim 10 wherein the chamber has a generally ovoid-cross-section.

* * * * *